Figure 3:
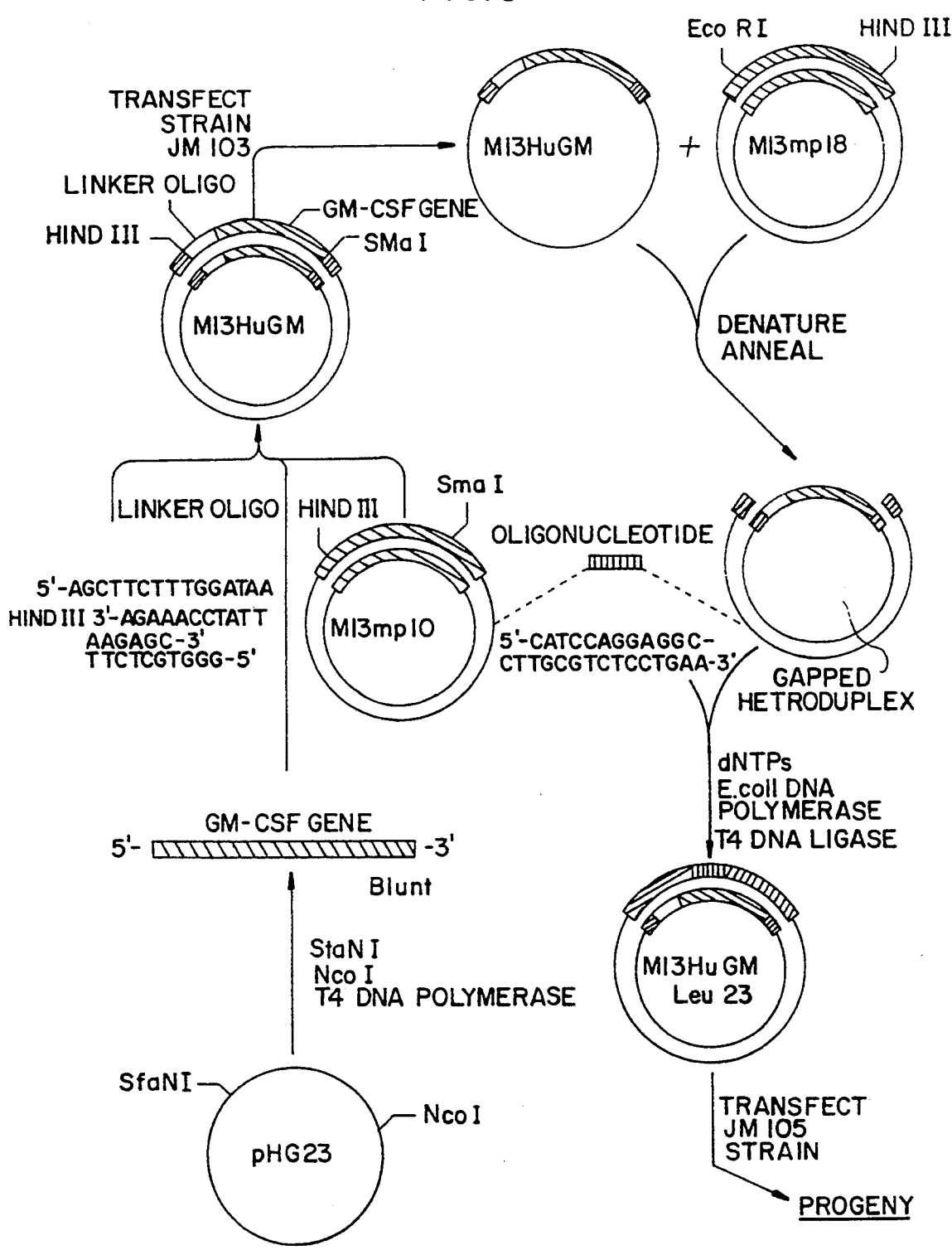

United States Patent [19]

Deeley et al.

[11] Patent Number: 5,393,870
[45] Date of Patent: * Feb. 28, 1995

[54] ANALOGS OF HUMAN GRANULOCYTE-MACROPHAGE COLONY STIMULATING FACTOR

[75] Inventors: Michael C. Deeley; Virginia L. Price, both of Seattle, Wash.

[73] Assignee: Immunex Corporation, Seattle, Wash.

[*] Notice: The portion of the term of this patent subsequent to Jul. 20, 2010, has been disclaimed.

[21] Appl. No.: 67,934

[22] Filed: May 27, 1993

Related U.S. Application Data

[60] Continuation of Ser. No. 254,238, Oct. 6, 1988, Pat. No. 5,229,496, which is a division of Ser. No. 763,130, Aug. 6, 1985.

[51] Int. Cl.⁶ .............................................. C07K 13/00
[52] U.S. Cl. ...................................... 530/351; 530/395; 435/69.1; 435/69.5; 435/69.9; 930/145
[58] Field of Search ................ 530/351, 395; 930/145; 435/69.1, 69.5, 69.9

[56] References Cited

PUBLICATIONS

Beggs, "Transformation of yeast by a replicating hybrid plasmid", *Nature*, 275:104–08 (1978).

Moonen et al., "Increased biological activity of deglycosylated rh GM–CSF by yeast or animal cells", *PNAS*, 84:4428–31 (1987).

Bitter et al., "Secretion of foreign proteins from *S. cerevisiae* directed by α–factor gene fusions", *PNAS*, 81:5330–34 (1984).

Jones, "The Synthesis and Function of proteases in Saccharomyces", *Ann. Rev. Genet.*, 18:233–70 (1984).

*Primary Examiner*—Garnette D. Draper
*Assistant Examiner*—David L. Fitzgerald
*Attorney, Agent, or Firm*—Foley & Lardner

[57] ABSTRACT

Amplified expression of recombinant DNA products is achieved in hosts expressing proteases that cleave at multi-basic amino acid residues. To this end, cDNAs encoding granulocyte-macrophage colony stimulating factor (GM-CSF) are mutated such that one or both of the arginine residues at positions 23 and 24 of the protein product are deleted or replaced by non-basic amino acid residues. The GM-CSF analogs thus obtained maintain the activity of the wild-type protein.

8 Claims, 8 Drawing Sheets

FIG. IA

```
                  *⌐SfaN I
  10            30                  50                        70
CTGC AGC ATC TCT GCA CCC GCC CGC AGC ACA CAG CCC TGG GAG CAT GTG AAT GCC ATC
     Cys Ser Ile Ser Ala Pro Ala Arg Ser Thr Gln Pro Trp Glu His Val Asn Ala Ile
          90               110               130                    150
CAG GAG GCC CGG CGT CTC AAC CTG AGT AGA GAC ACT GCT GAG ATG AAT GAA ACA GTA GAA GTC ATC TCA GAA ATG
Gln Glu Ala Arg Arg Leu Asn Leu Ser Arg Asp Thr Ala Glu Met Asn Glu Thr Val Glu Val Ile Ser Glu Met
 20                         30                       40                              
       170              190                  210                       230
TTT GAC CTC CAG GAG CCG ACC TGC CTA CAG ACC CGG GAG CTG GAG CTG CGG GGC AGC CTC ACC AAG CTC
Phe Asp Leu Gln Glu Pro Thr Cys Leu Gln Thr Arg Glu Leu Glu Leu Arg Gly Ser Leu Thr Lys Leu
 50                              60                               70
         250                   270                  290                    310
AAG GGC CCC TTG ACC ATG ATG GCC AGC CAC TAC AAG CAG CAC TGC CCT CCA ACC CCG GAA ACT TCC TGT GCA ACC CAG
Lys Gly Pro Leu Thr Met Met Ala Ser His Tyr Lys Gln His Cys Pro Pro Thr Pro Glu Thr Ser Cys Ala Thr Gln
              80                         90
      330              350                  370
ATT ATC ACC TTT GAA AGT TTC AAA GAG AAC CTG AAG GAC TTT CTG CTT GTC ATC CCC TTT GAC TGC TGG GAG CCA GTC
Ile Ile Thr Phe Glu Ser Phe Lys Glu Asn Leu Lys Asp Phe Leu Leu Val Ile Pro Phe Asp Cys Trp Glu Pro Val
 100                         110                      120
 390                   410                  430                    450
CAG GAG TGA GAC CGG CCA GAT GAG GCT GGC CAA GCC GGG GAG CTG CTC TCT CAT GAA ACA AGA GCT AGA AAC TCA
Gln Glu End
      470                   490                510                       530
GGA TGG TCA TCT TGG AGG GAC CAA GGG GTG GGC CAC AGC CAT GGT GGG AGT GGC CTG GAC TGC CTG GCC ACA CTGA
                                               ⌐Nco I
       550                    570               590                  610
CCT GAT ACA GGC ATG GCA GAA GAA TGG GAT ATT TAT ACT GAC AAA TAC TGA TAT TAT ATA TTA TAT TTT AAA TAA TTT AAT
                       630                   650
TTA ATT TAA TTT AAT TTA ATT GAC TAA TTA CTA TTA TTACG
```

FIG. 1B

```
  -6    -11        10   *┌SfaN I        30                            50
AGCT TCT TTG GAT AAA AGA GCA CCC GCC CGC TCG AGC CCC AGC ACA CAG CCC TGG GAG CAT GTG AAT GCC ATC
     Ser Leu Asp Lys Arg Ala Pro Ala Arg Ser Pro Ser Thr Gln Pro Trp Glu His Val Asn Ala Ile
                     90                           110                      130                           150
CAG GAG GCC TTG CGT CTC CTG AAC CTG AGT AGA GAC ACT GCT GAG ATG AAT GAA ACA GTA GAA GTC ATC TCA GAA ATG
Gln Glu Ala Leu Arg Leu Leu Asn Leu Ser Arg Asp Thr Ala Glu Met Asn Glu Thr Val Glu Val Ile Ser Glu Met
 20                       30                         40                         230
                170                        190                         210
TTT GAC CTC CAG GAG CCG ACC TGC CTA CAG ACC CGC CTG GAG CTG TAC AAG CAG CAC CTG CGG GGC AGC CTC AAG CTC
Phe Asp Leu Gln Glu Pro Thr Cys Leu Gln Thr Arg Leu Glu Leu Tyr Lys Gln His Leu Arg Gly Ser Leu Lys Leu
        50                         60                                                       70
                250                       270                        290                           310
AAG GGC CCC TTG ACC ATG ATG GCC AGC CAC TAC AAG CAG CAC TGC CCT CCA ACC CCG GAA ACT TCC TGT GCA ACC CAG
Lys Gly Pro Leu Thr Met Met Ala Ser His Tyr Lys Gln His Cys Pro Pro Thr Pro Glu Thr Ser Cys Ala Thr Gln
                          80                           90
                330                          350                         370
ATT ATC ACC TTT GAA AGT TTC AAA GAG AAC CTG AAG GAC TTT CTG CTT GTC ATC CCC TTT GAC TGC TGG GAG CCA GTC
Ile Ile Thr Phe Glu Ser Phe Lys Glu Asn Leu Lys Asp Phe Leu Leu Val Ile Pro Phe Asp Cys Trp Glu Pro Val
100                        110                       120
  390                          410                         430                              450
CAG GAG TGA GAC CGG CCA GAT GAG GCT GGA CAA GGG GTG GGC CAC AGC CAT GGT GGG AGT GGC CTG GAC TGC CTG GAC
Gln Glu End
                          470                          490                         510                  530
GGA TGG TCA TCT TGG AGG GAC CAA GAA TGG GAT ATT TAT ACT GAC AAA TAC TGA TAT TAT ATA TTA TAT TTT AAA TAA
                   550                          570                       590  ⌐NcoI                    610
CCT GAT ACA GGC ATG GCA GAA GAA TGG GAT ATT TAT ACT GAC AAA TAC TGA TAT TAT ATA TTA TAT TTT AAA TAA TTT
                         630                           650
TTA ATT TAA TTT AAT TTA ATT GAC TAA TTA CTA TTA TTACG
```

FIG. IC

```
     -6       -11        10       *—StaN I   30                        50                                            70
     AGCT TCT TTG GAT AAA AGA GCA CCC GCC CGC TCG CCC AGC ACA CAG CCC TGG GAG CAT GTG AAT GCC ATC
          Ser Leu Asp Lys Arg Ala Pro Ala Arg Ser Pro Ser Thr Gln Pro Trp Glu His Val Asn Ala Ile
                              90                             110                         10             130

CAG GAG GCC CGT CTC CTG AGT AGA GAC ACT GCT GAG ATG GCT GAA ACA GTA GAA ATG TCA GAA ATG
     Gln Glu Ala Arg Leu Leu Ser Arg Asp Thr Ala Ala Glu Met Asn Glu Thr Val Glu Val Ile Ser Glu Met
     20                              30                             40
         150                              170                 190                       210

TTT GAC CTC CAG GAG CCG ACC TGC CTA CAG ACC CGC CTG TAC AAG CAG GGC CTG CGG GGC AGC CTC ACC AAG CTC
     Phe Asp Leu Gln Glu Pro Thr Cys Leu Gln Thr Arg Leu Tyr Lys Gln Gly Leu Arg Gly Ser Leu Thr Lys Leu
                    50                           60                                70
         230                              250                      270                   290

AAG GGC CCC TTG ACC ATG ATG GCC AGC CAC TAC AAG CAG CAC TGC CCT CCA ACC CCG GAA ACT TCC TGT GCA ACC CAG
     Lys Gly Pro Leu Thr Met Met Ala Ser His Tyr Lys Gln His Cys Pro Pro Thr Pro Glu Thr Ser Cys Ala Thr Gln
     310                              80                                 350                              370
                                           330                                                90

ATT ATC ACC TTT GAA AGT TTC AAA GAG AAC CTG AAG GAC TTT CTG CTT GTC ATC CCC TTT GAC TGC TGG GAG CCA GTC
     Ile Ile Thr Phe Glu Ser Phe Lys Glu Asn Leu Lys Asp Phe Leu Leu Val Ile Pro Phe Asp Cys Trp Glu Pro Val
                    100                             110                              120
          390                              410                       430                  450

CAG GAG TGA GAC CGG CCA GAT GAG GCT GGC CAA GCC GGG GAG CTG CTC TCT CAT GAA ACA AGA GCT AGA AAC TCA
     Gln Glu End
               470                           490                          510                       530

GGA TGG TCA TCT TGG AGG GAC CAA GGG GTG GGC CAC AGC CAT GGT GGG AGT GGC CTG GAC TGC CTG GCC ACA CTGA
                    550                          570 └—NcoI              590                      610

CCT GAT ACA GGC ATG GCA GAA GAA TGG GAT ATT TAT ACT GAC AAA TAC TGA TAT TAT ATA TTA TAT TTT AAA TAA TTT AAT
                    630                               650

TTA ATT TAA TTT AAT TTA ATT GAC TAA TTA CTA TTA TTACG
```

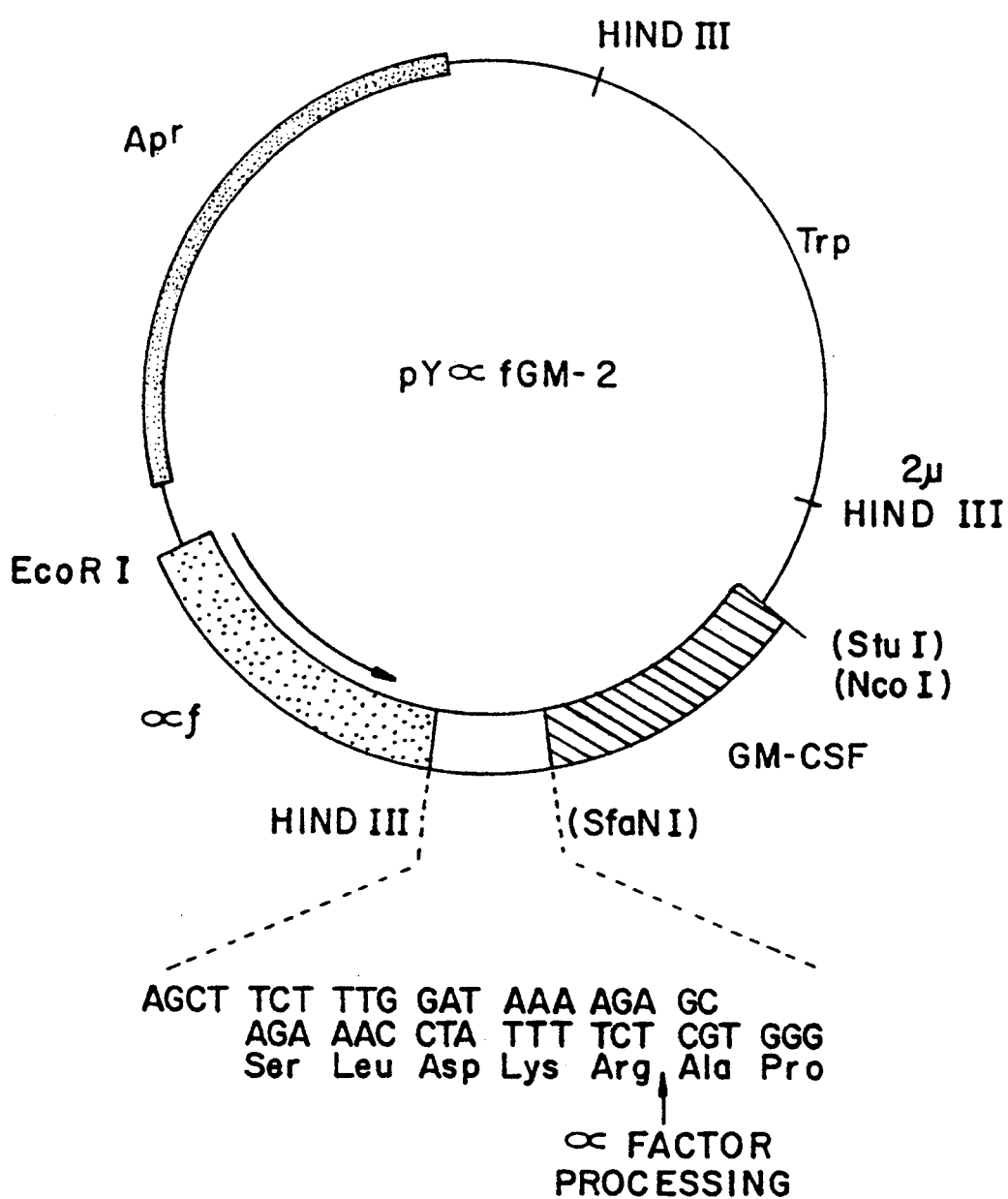

ANALOGS OF HUMAN GRANULOCYTE-MACROPHAGE COLONY STIMULATING FACTOR

This application is a continuation of application Ser. No. 07/254,238, filed Oct. 6, 1988, now U.S. Pat. No. 5,229,496, which is a divisional of Ser. No. 06/763,130, filed Aug. 6, 1985, which application is pending.

TECHNICAL FIELD

The present invention relates to a method for amplifying the expression of recombinant DNA in hosts expressing protease that cleave at multibasic amino acid residues and to the use of this method in conjunction with colony stimulating factor (hereinafter "CSF") and, more particularly human granulocyte-macrophage colony stimulating factor (hereinafter "GM-CSF").

BACKGROUND OF THE INVENTION

CSF refers to a family of lymphokines which induce progenitor cells found in the bone marrow to differentiate into specific types of mature blood cells. The particular type of mature blood cell that results from a progenitor cell depends upon the type of CSF present. For instance, erythropoietin is believed to cause progenitor cells to mature into erythrocytes, while thrombopoietin is thought to drive progenitor cells along the thrombocytic pathway. Similarly, granulocytemacrophage colony formation is dependent on the presence of GM-CSF. The present invention concerns an analog of human GM-CSG.

CSF, including human GM-CSF, is produced only in minute quantities in vivo. CSF-like factors have been extracted from body organs, Sheridan and Stanley, *J. Cell. Physiol.*, 78:451–459 (1971), and have been detected in serum and urine, Robinson et al., *J. Cell. Physiol.*, 69:83–92 (1967); Stanley et al., *J. Lab. Clin. Med.*, 79:657–668 (1972). Researchers have reported isolating low titer CSF-like factor from human peripheral blood cells which appear to be macrophages or monocytes, Moore and Williams, *J. Cell. Physiol.*, 80:195–206 (1972); Golde and Kline, *J. Clin. Invest.*, 51:2981–2983 (1972); Moore et al., *J. Natl. Cancer Inst.*, 50:591–601 (1973).

Although the factors identified by the above researchers have been reported to be CSF, heretofore sufficient quantities of homogeneous human CSF, including GM-CSF, have not been available to thoroughly investigate its biochemistry and biology. The availability of adequate quantities of homogeneous human GM-CSF would be valuable in investigations and possible treatment of proliferative blood disorders, such as certain leukaemias and anaemias. Also, human GM-CSF in greater purity and larger quantities than heretofore available could prove useful in achieving successful bone marrow transplantation following cancer chemotherapy.

One potential method of providing larger quantities of homogeneous polypeptides including human GM-CSF than heretofore available is through recombinant DNA techniques. Recombinant DNA techniques have been developed for economically producing a desired protein once the gene coding for the protein has been isolated and identified. A discussion of such recombinant DNA techniques for protein production is set forth in the editorial and supporting papers in Vol. 196 of *Science* (April 1977).

SUMMARY OF THE INVENTION

Genes encoding various protein products have been isolated and cloned for expression of functional protein product in yeast expression systems employing the promoter and leader sequence for the yeast pre-pro-α mating factor ("α-factor"). Although larger quantities of mature, homogeneous protein product were achieved through the yeast expression system than heretofore produced, applicants hypothesized that the level of protein product being recovered was possibly somehow being restricted by the existence of a potential cleavage site for the protease encoded by the KEX 2 gene of the yeast *Saccharomyces cerevisiae* ("*S. cerevisiae*"). This secretory pathway processing enzyme was found to cleave at "double basic amino acid residues," i e. two adjacent basic amino acid residues located along the amino acid sequence of the protein product. In an attempt to increase the levels of mature protein product recovered in yeast systems, applicants sought to alter wild-type genes to eliminate "multibasic amino acid residues," i.e., two or more adjacent basic amino acid residues located along the amino acid sequence of the protein product, by substitution or deletion of codons encoding multibasic residues.

The present invention has been carried out with respect to GM-CSF. Different types of CSF, including GM-CSF have been discussed supra. Although a substantial portion of the remainder of the application discusses present invention with respect GM-CSF, it is to be understood that the present invention is not limited to GM-CSF, but rather may be employed in conjunction with virtually all protein products that naturally are composed of multibasic amino acids. In addition, the present invention is not limited to the use of yeast cells as hosts, but rather is applicable to any host that expresses a protease that cleaves precursor protein products at double basic amino acid residues during the expression process.

An analog GM-CSF is produced by altering the wild-type gene for GM-CSF by replacing the applicable codons coding for basic amino acids to eliminate multibasic amino acids. One possible and preferred technique of making this substitution is by site-specific in vitro mutagenesis, for instance as discussed in Craik, *Biotechniques*, January 1985, 12–19. In this procedure, the gene coding for human GM-CSF is ligated into an M13 single-stranded filamentous phage vector which is then employed to transform an appropriate host to produce replicate single-stranded DNA templates. The single-stranded DNA templates are annealed with portions of a complementary M13 strand to form a gapped heteroduplex. A synthesized mutagenesis oligonucleotide constructed with the altered/replaced codon, is annealed to the corresponding portion of the wild-type GM-CSF gene disposed in the single-stranded region of the gaped heteroduplex. The gaps between the ends of the mutation oligonucleotide and the complementary M13 strand are enzymatically repaired to form a double stranded structure which is then used to transform an appropriate host. Properly mutagenized genes are detected by use of a radiolabeled oligonucleotide probe having the same structure as the mutagenesis oligonucleotide.

Thereafter, the nucleotide sequence of candidates identified with the radiolabeled probe is determined to verify the desired gene construction had been achieved. Next, the altered gene is transferred from the M13 vector to a yeast expression vector used to transform *S. cerevisiae* for expression of mature, analog GM-CSF. Biological assays are conducted to confirm that the analog GM-CSF exhibited substantially the same activity as the natural GM-CSF product.

An analog GM-CSF is also produced by altering the wild-type gene encoding GM-CSF by removing the applicable codons encoding basic amino acids to eliminate the occurrence of multibasic amino acid residues. As an illustrative but non-limiting example, the applicable codons may be deleted from the wild-type gene by the same site-specific in vitro mutagenesis technique discussed above regarding the replacement of codons encoding basic amino acid residues. In this procedure, the composition of the synthesized mutagenesis oligonucleotide is the same as the corresponding portion of the wild-type gene, however with the applicable codon or codons encoding the basic amino acid(s) deleted. With this exception the procedures for preparing recombinant DNA encoding the analog GM-CSF, for expression of the analog product and for biological assay to confirm the functionality of the analog GM-CSF is the same as discussed above.

BRIEF DESCRIPTION OF THE DRAWINGS

The details of typical embodiments of the present invention will be described in connection with the accompanying drawings, in which:

FIG. 1A illustrates the amino acid and nucleotide sequences of the wild-type human GM-CSF gene, including part of the 3′ non-coding region of the gene;

FIG. 1B illustrates the amino acid and nucleotide sequences of a mutant human GM-CSF gene wherein at least one codon coding for a basic amino acid residue has been replaced by a codon encoding for a nonbasic amino acid residue so that the analog GM-CSF encoded by the mutant gene is devoid of multibasic residues;

FIG. 1C illustrates the amino acid and nucleotide sequences of a mutant human GM-CSF gene wherein at least one codon encoding a basic amino acid residue has been deleted so that the analog GM-CSF encoded by the mutant gene is devoid of multibasic amino acid residues;

FIG. 2 illustrates the plasmid pYα fGM-2 used to direct expression of the wild type GM-CSF in yeast hosts;

FIG. 3 illustrates the strategy employed for generating the mutated, codon substituted gene, M13HuGMLeu23, coding for analog human GM-CSF;

FIG. 4 illustrates the pYα fHuGMLeu23 expression plasmid with the coding region for the mutated GM-CSF gene, M13HuGMLeu23, inserted therein for use in transforming host cells for amplified expression of functional analog human GM-CSF;

FIG. 5 illustrates the strategy employed for generating the mutated, codon deleted gene M13HuGM Δ Arg23 encoding analog GM-CSF; and, FIG. 6 illustrates the pY fHuGM Δ Arg23 expression plasmid with the coding region for the mutated GM-CSF gene, M13HuGM Δ Arg23, inserted therein for use in transforming host cells amplified expression of functional analog GM-CSF.

DETAILED DESCRIPTION OF THE PREFERRED EMBODIMENTS

Isolation of the Wild-Type Human GM-CSF Gene

The wild-type gene coding for human GM-CSF has been isolated and characterized. The nucleic acid sequence of the gene is shown in FIG. 1. This wild-type gene, inserted into a cloning plasmid, designated as pHG23 and then transformed into *E. coli*, is on deposit with the American Type Culture Collection ("ATCC"), 12301 Parklawn Drive, Rockville, Md. 20852, USA, under Accession No. 39900. Also, the wild type gene as inserted into a yeast expression plasmid, designated as pYα fGM-2, as shown in FIG. 2, is on deposit with the ATCC under Accession No. 53157.

In brief summary, the gene coding for wild-type human GM-CSF was isolated from a cDNA library with a nick-translated cDNA probe. The probe was isolated from a murine GM-CFSF cDNA library by use of a synthetic oligonucleotide probe corresponding to a portion of the nucleotide sequence of murine GM-CSG. Total human RNA was extracted from the HUT-102 lymphoma T-cell line and from peripheral blood T-lymphoma cells, and then polyadenylated mRNA was isolated from the total RNA extract. A cDNA library was constructed by reverse transcription of the polyadenylatedmRNA with the enzyme reverse transcriptase. The DNA was rendered double-stranded with DNA polymerase I and inserted into an appropriate cloning vector. Recombinant cloning vectors were used to transform an appropriate host.

Transformed hosts were identified and grouped into pools. Plasmid DNA prepared from these pools was hybridized with the murine cDNA probe that had been radiolabeled. The pool(s) of clones that gave a positive signal to the probe were identified and then the putative pools subdivided and a hybridization screen repeated. A single transformant corresponding to the wild-type human GM-CSF gene was eventually identified. Plasmid DNA was prepared from this transformant and characterized by DNA sequencing. The coding region of the wild-type human GM-CSF gene was employed to construct an expression plasmid designated as pYα fGM-2 and illustrated in FIG. 2, for use in a yeast host system to express mature GM-CSF. The expression plasmid was constructed with the yeast pre-pro-α mating factor ("α-factor") as an efficient promoter together with leader sequences to direct the synthesis and secretion of GM-CSF in yeast. A synthesized oligonucleotide, defined in FIG. 2, containing a 5′ cohesive terminal and a second α-factor processing site was coupled to the 5′ end of the GM-CSF gene to facilitate plasmid construction and improve expression levels. Thereafter, biological assays were conducted which confirmed that the expressed protein product was GM-CSF. The assay ascertained the ability of the GM-CSF to direct the formation of mixed, granulocytic-and macrophage-type colonies from human bone marrow cells. The GM-CSF was found to direct synthesis of GM-CSF activity in the bone marrow colony assay at a level of approximately $1.25\times10^6$ colony forming units ("CFU") per ml of culture supernatant.

Cloning of GM-CSF Gene Mutated by Codon Substitution.

In accordance with one aspect of the present invention, a mutated human GM-CSF gene is prepared by replacing codons encoding basic amino acid residues with codons encoding nonbasic amino acid residues. The mutated gene is cloned for use in the expression of analog GM-CSF that is devoid of multibasic amino acid residues. In one specific form of the present invention, the codon encoding amino acid residue No. 23, arginine, in the wild-type gene has been substituted with a codon encoding a nonbasic amino acid residue thereby eliminating the multibasic sequence arginine-arginine at amino acid residues Nos. 23 and 24 of the GM-CSF, FIG. 1A. The replacement residue may be composed of any nonbasic amino acid residues; however, the replacement residue chosen should not result in the creation of an enzyme cleavage site resulting in the undesirable cleavage of the GM-CSF expression product. Preferably, the replacement amino acid residue may include leucine or any other amino acid except lysine. Ideally, the replacement amino acid is composed of leucine.

It is to be understood that rather than replacing the arginine at amino acid residue No. 23 with a nonbasic residue, it is also within the scope of the present invention to instead replace the arginine at amino acid residue No. 24 with an appropriate nonbasic amino acid, for instance, with one of the amino acids set forth above. In addition, both arginine residues Nos. 23 and 24 could be replaced with nonbasic amino acid residues. An essential criterion regarding the particular amino acid residue(s) that is replaced is that the replacement result in the elimination of multibasic amino acids while substantially maintaining the biological activity of the GM-CSF.

Ideally the codon encoding of the nonbasic amino acid residue is chosen for maximum gene expression by host cells. It is known that in *S. cerevisiae* products encoded by genes composed of specific codon compositions are expressed more highly than products encoded by the same gene with an alternative codon composition for a particular amino acid residue. As a specific example, highly expressed genes in *S. cerevisiae* contain the TTG codon 92% of the time when encoding a leucine residue, and the other five leucine encoding codons only 8% of the time. Thus, in GM-CSF if the replacement residue is leucine, ideally the codon TTG will be employed.

The analog GM-CSF of the present invention preferably is produced by recombinant DNA methods employing a mutated GM-CSF gene coding for the analog protein product. In one preferred form of the present invention, the mutated gene is produced by substituting codon(s) encoding the desired nonbasic amino acid residue in place of codon(s) encoding the target basic amino acid residue(s). Various site-specific mutagenesis procedures may be used for making this substitution including oligonucleotide-directed site-specific mutagenesis techniques, as discussed generally by Craik, supra. One method utilizes a synthetic oligonucleotide-defined sequence which is complementary to the region of the cloned DNA molecule except for the one to several desired nucleotide mismatches. The synthesized oligonucleotide is annealed with a single-stranded template clone (+) of the original (wild-type) DNA molecule carried in a phage vector. Even though the synthesized oligonucleotide does not perfectly correspond with the single-stranded template clone, it will anneal under proper (nonstringent) hybridization conditions, especially if the mismatches are located at or near the middle of the oligonucleotide rather than at one of the ends. The mismatched oligonucleotide serves as a primer for DNA polymerase to synthesize the remainder of the complementary (−) strand, resulting in a double-stranded molecule which is employed to transform an appropriate host for the repair of the mismatches and to produce both the wild-type and mutant genes.

As a somewhat modified and preferred technique, the single-stranded DNA template (+) can be annealed with portions of a complementary (−) phage strand together with the synthesized mutagenesis oligonucleotide, thereby leaving gaps between the ends of the oligonucleotide and the complementary (−) strand fragment. These gaps are enzymatically filled, and then the gap-filled duplexed DNA is transformed into an appropriate host for replication of the mutant gene.

Other site-specific mutagenesis techniques also may be employed in conjunction with the present invention to substitute for codons coding for multibasic amino acids in the GM-CSF gene. For instance, methods have been developed for generating single-stranded regions in double-stranded DNA molecules to allow annealing of a mutator oligonucleotide to the sequence of interest. One such technique involves making a single-stranded nick in the plasmid DNA with a restriction endonuclease in the presence of ethidium bromide and then extending the nick into a gap with *Micrococcus luteus* DNA polymerase. Shortle et al., *Proc. Nat. Acad. Sci.* (USA), 79:1588–1592 (1982). A mutated oligonucleotide can then be annealed to the single-stranded portion of the plasmid, and the gaps at the ends of the oligonucleotide enzymatically repaired.

As a further alternative "gapped duplexes" can be prepared from double-stranded DNA molecules by the controlled digestion of a nicked or linearized plasmid with exonuclease III. Wallace et al., *Nucl. Acids Res.*, 9:3647–3658 (1981); and, Dalbadie-McFarland et al., *Proc. Nat. Acid. Sci.* (USA), 79:6409–6413 (1982).

Preparation of Single-Stranded DNA Template

Single-stranded DNA templates corresponding to the wild-type GM-CSF gene are prepared by cloning the wild-type gene in phage vectors capable of producing single-stranded DNA molecule product when double-stranded replicative form DNA is used as a cloning vector. One such strain of phage is M13. See Hu and Messing, *Gene*, 17:271–277; and, Messing, *Methods In Enzymology*, 101:20–78 (1983). The replicative form DNA phage cloning vector preferably is constructed with duplexed oligonucleotides attached to the 5′ terminal of the GM-CSF gene for use in linking the mutated GM-CSF gene to the α-factor promoter and leader sequences contained in the expression plasmid employed to express the mutated GM-CSF gene, as discussed infra. An example of such duplexed oligonucleotides is shown in FIG. 3. Ideally, the duplexed oligonucleotides together form a second α-factor processing site at the 3′ end of the oligonucleotide adjacent the 5′ end of the GM-CSF gene to improve expression levels.

The phage vector, with the duplexed linking oligonucleotide and the wild-type GM-CSF gene inserted therein, is used to transfect an appropriate bacteria host, such as various strains of *E. coli*. Typical *E. coli* strains that may be used in conjunction with the present invention include strains JM101, JM103, JM105, and JM107 of *E. coli* K12 (Bethesda Research Laboratories, Bethesda, Md.).

Preparation of Oligonucleotide

The oligonucleotide containing the desired codon substitution from the wild-type GM-CSF gene may be readily synthesized by well-known techniques, such as by phosphodiester or triester methods. The details of the triester synthesis technique are set forth, for example, in Sood et al., *Nucl. Acid Res.*, 4:2557 (1977); and, Hirose et al., *Tet. Lett.*, 28:2449 (1978).

Preferably, the substituted codon is located at approximately the center of the oligonucleotide, and the oligonucleotide is long enough to readily hybridize to the single-stranded DNA as prepared above, while being short enough to be relatively easily synthesized. As an illustrative but nonlimiting example, if, as discussed above, the arginine amino acid residue No. 23 of the wild type GM-CSF gene is substituted with leucine, then the oligonucleotide, designated MCD5-27, could be of the following composition: 5'-CATCCAG-GAGGCCTTGCGTCTCCTGAA-3'. In this oligonucleotide construction the codon corresponding to leucine, TTG, as underlined, is located near the center of the oligonucleotide. As noted above, this particular composition of the codon encoding leucine was chosen to maximize analog GM-CSF expression. It is to be understood that a smaller number of larger number of flanking nucleotides may be employed, and that the substitute codon does not necessarily have to be located at this position of the oligonucleotide.

Cloning of Mutated Gene

Referring to FIG. 3, for use in forming the heteroduplex DNA, double stranded wild-type M13 DNA ideally, but not necessarily, is prepared from the same strain used to form the single-stranded template. Preferably, the double stranded DNA overlaps substantially the entire template strand (+) except in the region of the substituted codon.

The wild-type M13 DNA portion and the oligonucleotide are annealed with the template strand (+) by well-known standard procedures to form the gapped duplex structure. The gaps between the ends of the oligonucleotide and the corresponding ends of the complementary (−) strand are filled in by standard techniques employing E. coli DNA polymerase ("Klenow" fragment) and T4 DNA ligase. Thereafter the covalently closed heteroduplex is employed to transform an appropriate host, such as a strain of E. coli. Upon transfection of the host and replication of the heteroduplex, mixed progeny containing either the wild-type or mutant copies of the GM-CSF gene are produced.

Screening of Cloned DNA Molecules

Plaques resulting from the transfection of the host are screened for the oligonucleotide-directed mutant DNA molecules with a radiolabeled oligonucleotide probe, ideally of the same composition as the mutation oligonucleotide. Although the oligonucleotide probe may be radiolabeled by many different techniques and with many different isotopes, of preference is the radiolabeling of the probe with T4 polynucleotide kinase and $^{32}$P-ATP. A standard protocol for the labeling procedure is set forth in Maniatus et al., *Molecular Cloning, a Laboratory Manual*, Cold Spring Harbor Laboratory, Cold Spring, N.Y. (1982).

Putative plaques are picked and screened with the $^{32}$P-labeled oligonucleotide probe. The picked plaques are used to inoculate microtiter wells containing YT medium. After a suitable growth period, the candidate cultures are spotted onto nitrocellulose filters placed on YT plates. After further growth, the DNA is liberated and bound to the nitrocellulose filter. The bound DNA is then hybridized with the labeled oligonucleotide probe. The specific DNA fragments that hybridize to the probe are identified by autoradiography. By this procedure candidates containing the site-specific mutation are identified. Single-stranded phage and double-stranded replicative form DNA containing the site-specific mutation, designated as M13HuGMLeu23, are prepared.

Characterization of Screened GM-CSF Mutation

The single-stranded phage DNA prepared above is sequenced using standard chain-termination methods. This technique of nucleotide sequencing was originated by Sanger et al., *Proc. Natl. Acad. Sci. (USA)*, 70:5463 (1977). See U.S. Pat. No. 4,322,499. Methods for chain-termination sequence determination are set forth in: the Amersham Handbook entitled, *M13 Cloning and Sequencing*, Blenheim Cresent, London (1983) (hereinafter "Amersham Handbook"); Messing, 2 *Recombinant DNA Technical Bulletin, NIH Publication No. 79–99*, 2, 43–48 (1979); Norrander et al., *Gene*, 26:101 (1983); Cerretti et al., *Nucl. Acids Res.*, 11:2599 (1983); and, Biggin et al., *Proc. Natl. Acad. Sci. (USA)*, 80:3963 (1983).

In the chain-termination sequencing method, single-stranded template molecules are primed with a short universal primer strand having a free 3' hydroxyl group and then using DNA polymerase (Klenow fragment) to copy the template strand in a chain extension reaction using all four deoxyribonucleotide triphosphates, i.e., dATP, dCTP, dTTP (collectively referred to as "dNTPs"), with one of the dNTPs being radiolabeled. In the synthesis reaction, a nucleotide specific chain terminator lacking a 3'-hydroxyl terminus, for instance, a 2', 3' dideoxynucleotide triphosphate ("ddNTP"), is used to produce a series of different length chain extensions. The terminator has a normal 5' terminus so that it can be incorporated into a growing DNA chain, but lacks a 3'-hydroxyl terminus. Once the terminator has been integrated into a DNA chain, no further deoxynucleotide triphosphates can be added so that growth of the chain stops. Four separate synthesizing reactions are carried out, each having a ddNTP of one of the four nucleotide dNPTs, i.e., dATP, dCPT, dGTP and dTTP. One of the normal dNTPs is radiolabeled so that the synthesized strands, after having been sorted by size on a polyacrylamide gel, can be autoradiographed. The chain extensions from the four reactions are placed side by side in separate gel lanes so that the pattern of the fragments from the autoradiography corresponds to the nucleic acid sequence of the cloned DNA.

FIG. 1B illustrates the nucleotide sequence of the mutated human GM-CSF gene contained in the M13HuGMLeu23 plasmid DNA. The corresponding amino acid composition of the coding region of the mutant gene is also illustrated in FIG. 1B, beginning from the Ala residue, No. 1 (nucleotide No. 14) and extending to the Glu residue, No. 127 (nucleotide No. 394). As expected the M13HuGMLeu23 mutant differed from the wild-type gene, FIG. 1A, only at the twenty-third codon in which the altered gene contained the sequence TTG (Leu) rather than CGG (Arg). In FIG. 1B, the nucleotides 5' of the coding region of the mutant gene compose the second α-factor processing site and a Hind III cohesive 5' terminal (nucleotide Nos. −6 to 13).

It is to be understood that rather than employing the chain-termination technique outlined above, other known methods may be utilized to sequence cloned human cDNA inserts without departing from the spirit or scope of the present invention. For instance, the chemical degradation method of Maxam and Gilbert as set forth in *Proc. Natl. Acad. Sci. (USA)*, 74:560 (1977) can be used.

Expression of Analog GM-CSF

Figure 4:
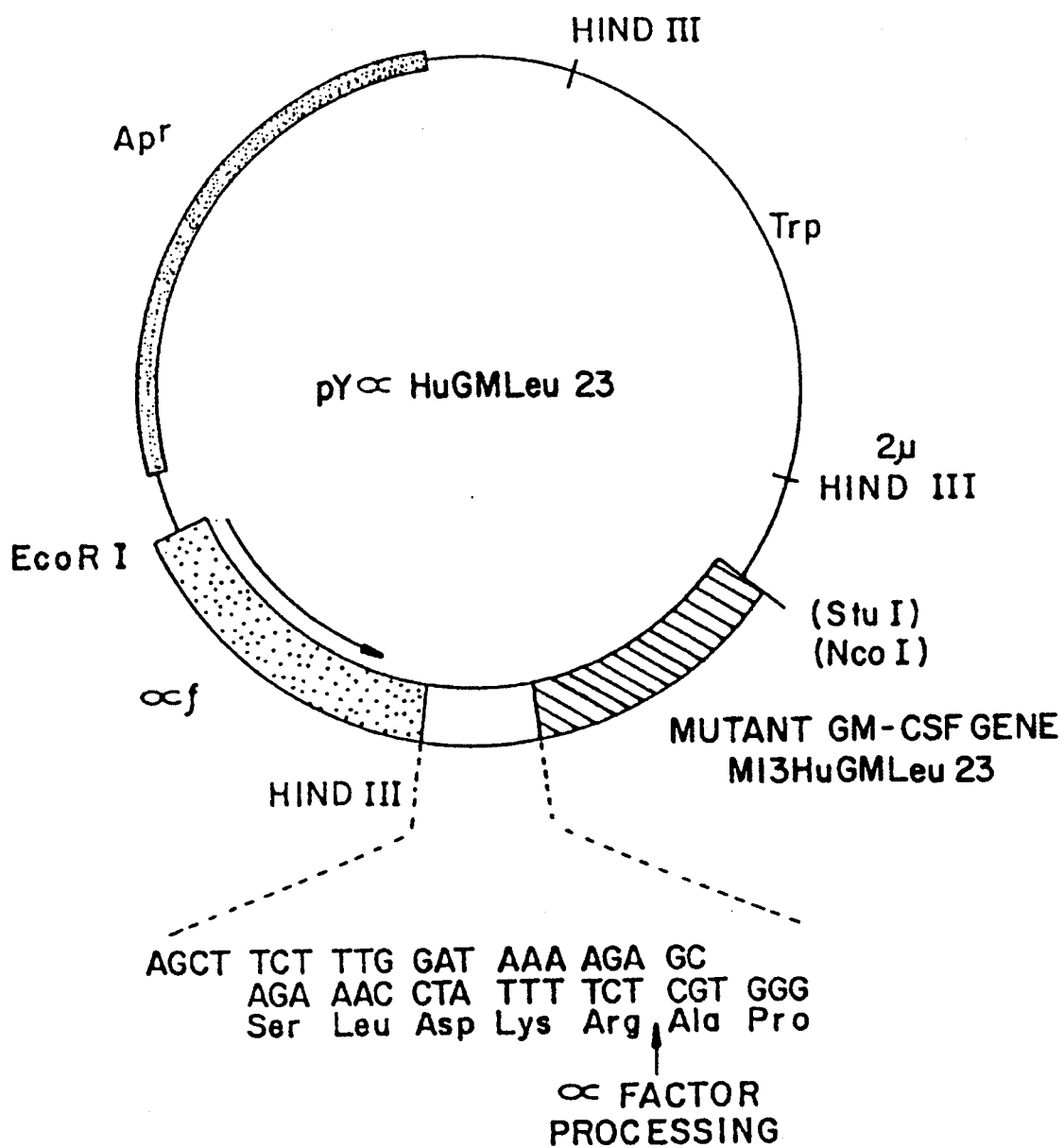

The M13HuGMLeu23 cDNA fragment shown in FIG. 1B, from the Hind III restriction site (nucleic acid No. −6) to Nco I restriction (nucleic acid No. 502) is inserted into an expression vector (see FIG. 4) designed to direct synthesis and secretion of the mature form of analog GM-CSF from yeast host cells. The expression vector, for instance pYα fHuGMLeu23, preferably contains sequences derived from plasmid pBR 322 containing an origin of replication and the ampicillin resistance gene (Amp$^r$) (thick line portion in FIG. 4). Preferably, the expression vector also includes sequences from yeast, for instance the tryptophan-1 gene (Trp-1) as a selectable marker and the 2 u yeast origin of replication (thin line portion in FIG. 3). Ideally, the expression vector further includes the yeast α-factor (for instance, stippled box portion) as an efficient promoter together with leader sequences to direct the synthesis and secretion of GM-CSF in yeast hosts, followed by the second α-factor processing site (open box portion) derived from the duplexed linking oligonucleotide and then the sequence for coding region of GM-CSF (hatched box portion). The structure of the α-factor gene is discussed in Kurjan and Herskowitz, *Cell*, 30:933–943 (1982).

The pYα fHuGMLeu23 expression plasmid is transformed into an appropriate strain of *S. cerevisiae*. Preferable strains include, but are not limited to, yeast strains 79, X2181-1B, DBY746, YNN282, 20B-12. These strains are all α, Trp 1 for compatibility with the α-factor promoter and for selection of Trp+ transformants. These strains are all widely available, for instance strain 79 is available from the Yeast Genetic Stock Center, Department of Bio-Physics and Medical Physics, University of California, Berkeley, Calif. 94702.

Transformation of the yeast host with the recombinant expression plasmid containing the mutated GM-CSF gene is conducted according to well known procedures wherein spheroplasts are formed and then washed prior to plasmid uptake. Standard protocols for this procedure have been established. See Beggs, *Nature (London)*, 275:104 (1978); Hinnen et al., *Proc. Natl. Acad. Sci. (USA)*, 75:1929 (1978).

The yeast culture supernatants are assayed for biological activity through their ability to direct the formation of mixed, granulocytic and macrophage-type colonies from human bone marrow cells. As a control, plasmid pYα f, of the same construction as pYα fHuGMLeu23 but lacking the GM-CSF sequences, was also transformed into a yeast host and the culture supernatant tested for biological activity. The pYα fHuGMLeu23 supernatant was found to direct synthesis of high levels of GM-CSF activity in the bone marrow colony assay ($7.2 \times 10^6$ CFU-C/ml): whereas, no activity was detected from the supernatant derived from the pYα f control plasmid.

Cloning, Screening and Characterization of GM-CSF Gene Mutated by Codon Deletion and Expression of Analog GM-CSF With Mutated Gene In accordance with another aspect of the present invention, a mutated human GM-CSF gene is prepared by deleting codons encoding basic amino acid residues, and the mutated gene is cloned for expression of analog GM-CSF that is devoid of multibasic amino acid residues. In one specific form of this aspect to the present invention, the codon encoding amino acid residue No. 23, arginine-arginine at amino acid residue Nos. 23 and 24 of the GM-CSF, FIG. 1A. It is to be understood that rather than deleting the arginine at amino acid residue No. 23, it is also within the scope of the present invention to delete the arginine at amino acid residue No. 24, or to delete both arginine residues at residue Nos. 23 and 24. An essential criterion regarding the particular amino acid residue(s) deleted is that the deletion result in the elimination of multibasic amino acids while maintaining the biological activity of the GM-CSF.

As in the above-discussed GM-CSF gene mutated by codon substitution, the analog GM-CSF employing the GM-CSF gene mutated by codon deletion preferably is produced by recombinant DNA methods. In one preferred form of the present invention, the mutated gene having codon(s) deleted is produced by the same site-specific mutagenesis technique discussed above relative to the GM-CSF gene mutated by codon substitution, with the exception that rather than synthesizing the oligonucleotide with a substituted, nonbasic amino acid codon, the oligonucleotide is prepared by deletion of one or more of the target codons encoding basic amino acid residues deleted. With this one exception, the same procedure discussed above for preparing the mutant gene by codon substitution is used to prepare the mutant gene by codon deletion. In the procedure the single-stranded DNA template (+) corresponding to the wild-type GM-CSF gene is prepared by cloning the wild-type gene in phage vectors capable of producing single-stranded DNA product when double-stranded replicative form DNA is used as a cloning vector. The single-stranded DNA template is annealed with portions of a complementary (−) phage stranded together with the synthesized, codon deleted mutagenesis oligonucleotide thereby leaving gaps between the ends of the oligonucleotide and the complementary (−) strand fragment. These gaps are enzymatically filled and then the gap-filled duplexed DNA is transformed into an appropriate host for replication of the codon deleted mutant gene.

As discussed above, the oligonucleotide containing the desired codon deletion from the wild-type GM-CSF gene is synthesized by well-known techniques, such as by phosphodiester or triester methods. Preferably the codon deletion is located at approximately the center of the oligonucleotide, and the oligonucleotide is long enough to readily hybridize to the single-stranded DNA template while being short enough to relatively easily synthesized. As an illustrative but nonlimiting example, if, as discussed above, the arginine amino acid residue No. 23 of the wild-type GM-CSF gene is deleted, then the oligonucleotide, designated as MCD5-24, could be of the following composition: 5′-CATCCAGGAGGCCCGTCTCCTGAA-3′, It is to be understood that a smaller or larger number of flanking nucleotides may be employed on either side of the location of the deleted codon.

The GM-CSF gene mutated by codon deletion is cloned and screened in the same manner discussed above relative to the gene mutated by codon substitution. Also, plasmid DNA designated as M13HuGM Δ Arg23, containing the deleted arginine residue at position No. 23, is sequenced using standard chain-termination methods as discussed above beginning at page 9. FIG. 1C illustrates the nucleotide sequence of the mutated GM-CSF gene contained in the M13HuGM Δ Arg 23 plasmid DNA. The corresponding amino acid composition of the coding region of the mutated gene is also illustrated in FIG. 1C, beginning with Ala residue (No. 1)(nucleotide No. 14) and extending to the Glu residue, No. 126 (nucleotide No. 391). As shown in FIG. 1C, the M13HuGM Δ Arg23 differs from the wild-type gene, FIG. 1A, only at the 23rd codon which was missing in the altered gene. The nucleotides 5′ of the coding region of the mutant gene are composed of the α-factor processing site and a Hind III cohesive 5′ terminal, as illustrated in FIG. 1C (nucleotide Nos. −6 to 13).

Analog GM-CSF is expressed with the mutant M13HuGM Δ Arg23 gene using the same procedure employed to express analog GM-CSF using the M13HuGMLeu23 mutant gene discussed above beginning at page 11. Also the expressed protein product is tested for biological activity using the same bone marrow assay discussed above.

The processes and products of the present invention are further illustrated by the following examples.

EXAMPLE 1

Preparation of Single-Stranded DNA Template

As shown in FIG. 3, a 487 base pair DNA fragment containing the coding region and a portion of the 3' flanking region of the human GM-CSF gene (extending from nucleotide No. 16 to nucleotide No. 502 in FIG. 1A) was isolated from the pHG23 plasmid by digestion with the restriction enzymes Sfa NI and Nco I. T4 DNA polymerase was employed to blunt end the Nco I site of the gene fragment. Digestion of the pHG23 plasmid with the Sfa NI results in elimination of the first two nucleotides of the coding region of the GM-CSF gene. A duplexed linking oligonucleotide of the composition set forth below in Table 1 was synthesized to add back the two nucleotides of the initial Ala amino acid and also provides a second α-factor processing site for use in subsequent high level expression of the mutated GM-CSF gene in yeast hosts, as discussed more fully in Example 6. As shown in Table 1, the duplexed oligonucleotide is constructed with a cohesive Hind III 5' terminal.

TABLE I

```
5' AGCT  TCT  TTG  GAT  AAA  AGA   GC        -3'
3'       AGA  AAC  CTA  TTT  TCT /\ CGT GGG  -5'
         Ser  Leu  Asp  Lys  Arg |  Ala Pro
HIND III                         factor
                                 processing
```

The isolated GM-CSF gene fragment, together with the individual oligonucleotides composing the duplex shown in Table 1 are ligated into the strain mp10 of the M13 phage vector (Amersham, Arlington Heights, Ill.), which was previously digested with the Hind III and Sma I restriction enzymes. Ligation was accomplished in a reaction mixture composed of 20 nanograms (ng) of linearized mp10M13, 50 ng of the mutated GM-CSF gene fragment, 5 ng of synthetic oligonucleotides, one unit of T4 DNA ligase and sufficient T4 ligase buffer (0.4M Tris [ph 7.4], 0.1M MgCl$_2$, 0.1M dithiothreitol, 10 mM spermidine, 10mM ATP and 1 mg/microliter ("ul") BSA) to form a 20 ul reaction volume. Reaction was carried out by incubation at 25° C. for 15 hours.

The M13mp10 vector with the DNA fragment inserted therein, designated as M13HuGM, was used to transfect by standard protocol E. coli JM103 of the strain K12 (Bethesda Research Laboratories, Bethesda, Md.) to produce a strain of E. coli actively excreting M13HuGM phage containing Single stranded DNA was isolated from the phage by extraction with phenol:chloroform according to standard protocol as detailed in the Amersham Handbook.

EXAMPLE 2

Oligonucleotide Synthesis and Radiolabeling

The oligonucleotide employed for site-directed mitogenesis of the GM-CSF gene by codon substitution was chemically synthesized by standard triester method, as detailed by Sood et al., supra and Hirose et al. supra. The oligonucleotide, designated as MCD5-27, was composed of the following sequence: 5'-CATCCAG-GAGGCCTTGCGTCTCCTGAA-3'. The oligonucleotide was deblocked and purified by Sepyhadex G-50 chromatography (Pharmacia Fine Chemicals) followed by preparative gel electrophoresis.

The oligonucleotide was terminally radiolabeled with $^{32}$P for use as a screening probe. To facilitate radiolabeling, the 5' ends of the oligonucleotides were synthesized with OH termini, thereby eliminating the phosphatase treatment, which typically must be employed when labeling DNA fragments. The labeling protocol included adding 100 ng in 1 ul volume of the synthetic oligonucleotide to 16 ul of $^{32}$P-ATP (7000 Ci/mM), 1 ul (10 U) of T4 Polynucleotide kinase and 2 ul of 10×kinase buffer I (0.5M Tris-Cl [pH 7.0] 0.1 mM MgCl$_2$, 50 mM dithiothreitol, 1 mM ETDA). The reaction is carried out at 37° C. for 30 minutes, and then thereafter the $^{32}$P labeled oligonucleotides and unincorporated $^{32}$P-ATP were separated by Sephadex G-50 chromatography (Pharmacia Fine Chemicals).

EXAMPLE 3

Site-Directed Mutagenesis of GM-CSF by Codon Substitution

As illustrated in FIG. 3, for use in forming the gaped heteroduplex structure, strain mp18 of the M13 phage vector was digested with the restriction enzymes EcoRI and Hind III by standard techniques. The resulting major fragment and mutagenesis oligonucleotide MCD5-27 were annealed to the single-stranded template M13HuGM containing the wild type GM-CSF gene by the following procedure. One microgram ("ug") of the digested M13mp18 in double-stranded form was mixed with 0.5 ug of the single-stranded template DNA M13HuGM in 30 ul of 100 mM NaCl, 40 mM Tris-HCl (pH 7.5), 20 mM MgCl$_2$, 2.0 mM β-mercaptoethnol. The single-stranded template-double-stranded form M13mp18 fragment mixture was denatured by heating to 100° C. for 3 minutes and allowed to cool over 20 minutes to 65° C. Oligonucleotide MCD5-27 containing a 5'-phosphate (50.0 pmoles) was added and the mixture cooled slowly to 30° C. and then placed on ice for 15 minutes. Thereafter the following were added to the mixture: 70 ul of 22 mM Tris-HCl (pH 7.5), 11 mM MgCl$_2$, 1.0 mM α-mercaptoethanol, 0.83 mM dATP, 0.83 mM dCTP, 0.83 mM dGTP, 0.83 mM dTTP, 0.4 mM rATP, 0.5 units of E. coli DNA polymerase (Klenow fragment) (Boehringer Mannheim Biochemicals), and 0.5 units T4 DNA ligase (Bethesda Research Laboratories). After an additional 30 minutes at 0° C., this primary extension mixture was incubated at 14.5° C. for 20 hours.

EXAMPLE 4

Screening for Mutated Gene

The gap-filled duplex structure from EXAMPLE 3 was employed to transfect competent JM105 E. coli cells (Bethesda Research Laboratories, Bethesda, Md.) by standard techniques, such as set forth in the Amersham Handbook, supra. The transfected JM105 cells were plated immediately after heat shock onto fresh YT plates in top agar.

Ninety-four of the resulting plaques were picked and screened with the radiolabeled MCD5-27 oligonucleotide probe, as prepared in EXAMPLE 2. The recombinant (white) plaques were picked with a sterile loop and used to inoculate microtiter dish wells containing 100 ul of YT medium. After about 5-7 hours growth at 37° C. a 96 well replicator was used to spot the candidate cultures onto nitrocellulose filters placed on YT plates, in duplicate. After overnight growth at 37° C., the filters were removed from the petri dishes. The DNA was liberated using alkali and neutralizing solutions by the general method as described by Maniatis et al., supra. After the transfer process, the filter was air dried and baked for 2 hours at approximately 80° C. to bind the single-stranded DNA to the nitrocellulose.

The bound DNA was next hybridized with the labeled oligonucleotide probe. Briefly, the baked nitrocellulose was incubated at 68° C. for 2-4 hours in prehybridization buffer composed of: 6× standard saline-citrate ("SSC") (1× SCC is 0.15M NaCl, 0.015M NaCitrate, pH 7.0); and, 5× Denhardt's solution (0.02% Ficoll, 0.02% polyvinylpyrrolidone, 0.2% bovine serum albumin). The filter was then incubated for 16 hours at 55° C. with the $^{32}$P-labeled oligonucleotide probe ($10^6$ cpm/ml, from EXAMPLE 2) in hybridizing buffer as above. After hybridization, the filter was washed extensively under high stringency conditions first with 6× SSC at room temperature and then for 1 hour at 68° C. in 0.6× SSC. After air drying, the filter was subjected to autoradiography at −70° C. This procedure resulted in clear identification of candidates containing the mutant GM-CSF gene, designated as M13HuGMLeu23.

EXAMPLE 5

Characterization of the Screened Mutagenized Gene

DNA templates were prepared from the candidates identified in EXAMPLE 4 and sequenced by standard chain-termination method as described in the Amersham Handbook, supra. The synthetic universal primer: 5'- CCCAGTCACGACGTT-3' (P-L Biochemicals, Milwaukee, Wis.), was annealed to the single-strand DNA templates and used to prime DNA synthesis as described above at page 10. Thereafter, the extension fragments were size-separated by gel electrophoresis and autoradiographed from which the nucleotide sequences of the fragments were deduced.

Deoxyadenosine 5' (α [$^{35}S$] thio) triphosphate (hereinafter "dATP [α-$^{35}S$]") was used as the radioactive label in the dideoxy sequencing reactions. Also, rather than using the gel set forth at page 36 of the Amersham Handbook, a 6% polyacrylamide gel was employed (6% polyacylmide gel, 0.4 mm thick, containing 7M, urea 100 mM Tris borate [pH 8.1], and 2 mM EDTA).

As noted above, the nucleotide sequence of the mutant GM-CSF gene, M13HuGMLeu23, is illustrated in FIG. 1B, with the mature protein beginning at the asterisk (*). The corresponding amino acid composition of the mature protein is set forth below the corresponding codons, beginning from the Ala residue, No. 1 (nucleotide No. 14) and extending to the Glu residue, No. 127 (nucleotide No. 394). As expected, this mutant gene differed from the wild type gene only at the 23rd codon in which the mutant gene contains the sequence TTG coding for leucine rather than the sequence CGT, coding for arginine. The nucleotides 5' from the mature gene constitute the second α-factor processing site and a Hind III cohesive 5' terminal, as illustrated in FIG. 3.

EXAMPLE 6

Expression of Analog GM-CSF

The coding region, together with a portion of the 3' flanking region of the mutant GM-CSF gene as set forth in FIG. 1B (nucleotides 14 through 502), and also together with the second α-factor processing site and 5' Hind III cohesive terminal as coupled to the 5' end of the analog GM-CSF gene, was removed from the mutagenesis vector and employed to form a recombinant expression plasmid, designated as pYα fHuGMLeu23 to direct analog GM-CSF expression in yeast host cells. As shown in FIG. 4, the pYα fHuGMLeu23 expression plasmid includes an origin of replication and an ampicillin resistant gene from plasmid pBR322 (thick line portion). The expression plasmid also includes the yeast 2u circle origin of replication and the Trp I gene for selection of transformed yeast hosts [Trp-auxotrophs] (thin line portion in FIG. 4). The expression plasmid further includes the α-factor promoter and leader sequences used to direct transcription and secretion of the analog GM-CSF (stippled box portion). The analog GM-CSF sequences are shown in hatched box portion in FIG. 4, whereas the Cathepsin B-like maturation site functioning as a second α-factor processing site is shown as an open box portion in FIG. 4, with the sequence thereof also set forth in FIG. 4.

The 5' leader sequence, the coding region and a portion of the 3' flanking region of the mutant GM-CSF gene, from nucleotide Nos. −6 to 502, was removed from the mutagenesis vector M13HuGMLeu23 and inserted into the expression vector pYα fHuGMLeu23 by digestion with the restriction enzyme Nco I followed by treatment with T4 DNA polymerase to fill in the recessed 3' end at the Nco I site with deoxynucleotides. Next the cleaved vector was treated with Hind III and the resulting 508bp M13HuGMLeu23 DNA fragment with the 5' leader sequence attached thereto was isolated by gel electrophoresis. This DNA fragment was ligated into the pYα f vector which previously had been prepared by removal of the Hind III-Stu I/Nco I section from the pYα fGM-2 expression plasmid (FIG. 2) (ATCC No. 53157) by standard techniques.

The pY' fHuGMLeu23 expression plasmid was transformed into yeast strain 79 (α, Trp 1-1, Leu 2-1) of *S. cerevisiae* for selection of Trp+ transformants by standard techniques. Prior to transformation, the strain 79 was grown in culture in YEPD medium (1% [wt/vol] yeast extract, 2% [wt/vol] peptone, 2% [wt/vol] glucose), to a density of $2\times10^7$ cells/ml. Cells were harvested by centrifugation at 1000×g for 5 minutes at 22° C., and then the resulting pellet was washed with sterile, distilled water.

The yeast cells were then concentrated by resuspending in 1/10 vol. of SED (1M sorbitol, 25 mM EDTA [pH 8.0], and 50 mM dithiothreitol) and incubating for 10 minutes at 30° C. The cell-buffer mixture was then centrifuged for 5 minutes at 300×g. The pellet was washed once with 1/10 vol. of 1M sorbitol and the cells resuspended in 20 milliliters of SCE (1M sorbitol, 0.1M sodium citrate [pH 5.8], 0.01M EDTA). Glusulase, to break down the cell walls, in an amount of $10^{-3}$ vol., was added to the solution and then the solution incubated at 30° C. for 30 minutes with occasional gentle shaking. The presence of spheroplasts was assayed by diluting 10 microliters of the yeast cells into a drop of 5% SDS (wt./vol.) on a microscope slide to observe for "ghosts" at 400×phase contrast. The cell mixture was then centrifuged at 300×g for 3 minutes. The resulting pellet was twice washed with 1/10 vol. of 1M sorbitol. The pellet was then once washed in CaS (1M sorbitol, 10 mM $CaCl_2$).

The yeast spheroplasts were then transformed with the previously prepared expression vector in a procedure adapted from Beggs, supra. The pelleted spheroplasts were suspended in 1/200 vol. of CaS and then divided into 100 microliter aliquotes in 1.5 ml Eppendorf tubes. Then, from 1 to 10 ul of the plasmid DNA were added to each aliquot (0.5 to 5 ug). The mixture was incubated at room temperature for 10 minutes and then 1 ml of PEG (20% PEG 4000, 10 mM $CaCl_2$, 10 mM Tris-HCl [pH 7.4]) was added to each aliquot to promote DNA uptake. After 10 minutes at room temperature, the mixture was centrifuged for 5 minutes at 350×g. The resulting pellet was resuspended in 150 ul of SOS (10 ml of 2M sorbitol, 6.7 ml of YEPD medium, 0.13 ml of 1M $CaCl_2$, 27 ul of 1% tryptophan and 3.7 ml of water). This mixture was incubated for 20 minutes at 30° C. The cells were then plated.

Prior to plating the protoplast/DNA mixture, selective plates were preincubated at 37° C. Three ml of melted top agar (45° C.), composed of 18.2 ml of sorbitol, 2 gm agar, 0.6 gm Difco yeast nitrogen base (without amino acids), 2 gm glucose, 0.1 ml of 1% adenine, 0.4 ml of 1% uracil and amino acids as required, was then added to each aliquot of transformed cells and the tube contents poured on the selective plates. The plates were incubated from 2 to 4 days at 30° C. Colonies which developed in the Trp minus medium contained plasmids that have the Trp 1 gene, i.e., those that are transformed.

Prior to biological assay, the transformants were grown in 20–50 ml of YEPD at 30° C. to stationary phase. At the time of harvest, the protease inhibitors phenyl methyl sulfonyl flouride (PMSF) and Pepstatin A were added to a final concentration of 1 mM and 10 uM, respectively. The cells were then removed by centrifugation at 400×g and the medium was filtered through a 0.45 micron cellulose acetate filter.

EXAMPLE 7

Colony Assay

The presence of analog GM-CSF harvested from the yeast cultures in Example 6 was confirmed by assaying the ability of the supernatant to stimulate growth of human bone marrow colonies in agar. For use in the assay, human bone marrow from the iliac crest of healthy donors was collected in a heparinized syringe. The marrow was diluted 1:3 with phosphate buffered saline (PBS) at room temperature and layered onto a solution of 54% percoll (Pharmacia Fine Chemicals). After centrifugation at 500×g at room temperature for 20 minutes, the interface was collected and washed with 20 volumes of PBS. The suspension was then centrifuged at 250×g for 10 minutes at room temperature. The cells were then resuspended in 10 ml of α-Minimal Essential Medium with nucleotides (α-Mem, Gibco) for cell counting and viability determination. FCS was then added and the cell suspension stored on ice until the assay was carried out.

In the assay, bone marrow cells as prepared above were added at a final concentration of $1 \times 10^5$ ml to an incubation medium consisting of: (a) seven parts of a solution containing 28.1% FCS, $0.7 \times 10^{-4}$M 2-mercapto-ethanol, 0.12 mg/ml asparagine, 0.7 mg/ml glutamine, 150 units of penicillin G, 150 units of streptomycin, 1.1×α-MEM with nucleotides, and 2.2×vitamins (Gibco); and, (b) three parts of 1.4% bacto-agar solution (Difco). The cultures were incubated in a humidified atmosphere at 37° C. in the presence of 5% $CO_2$. After seven to fourteen days of culture, the number and types of colonies, whether granulocyte, macrophage or mixed granulocyte-macrophage, were determined. Applicants found that the analog GM-CSF gene from the pYα fHuGMLeu23 clones directed synthesis of GM-CSF activity at the high level of $7.2 \times 10^6$ colony forming units ("CFU") per milliliter. This activity level was determined by multiplying by 50 the reciprocal of the dilution giving 50% of the maximum colony number. Applicants have found that the average number of colonies from $1 \times 10^5$ bone marrow cells was 73±16. The colonies formed at 14 days by the recombinant GM-CSF were well defined and consisted of three types: approximately ⅓ mixed granulocyte-macrophage colonies; approximately ⅓ tight granulocyte colonies, and approximately ⅓ dispersed macrophage colonies.

As a control for the expression system of the present invention, a plasmid identical to pYαfHuGMLeu23, but lacking the GM-CSF sequences, was also transformed into yeast strain 79. The culture supernatant from the yeast produced no GM-CSF activity in the bone marrow colony assay.

EXAMPLE 8

GM-CSF Gene Mutated by Codon Deletion

The oligonucleotides employed for site-directed mutagenesis of the GM-CSF gene by codon substitution is chemically synthesized by standard triester method, as detailed by Sood et al. supra and Hirose et al. supra. The oligonucleotide, designated as MCD5-24, is composed of the following sequence: 5'-CATCCAG-GAGGCCCGTCTCCTGAA- 3'. The oligonucleotide is deblocked and purified by Sephadex G50 chromatography (Pharmacia Fine Chemicals) followed by preparative gel electrophoresis. Thereafter, the oligonucleotide is terminally radiolabeled with $^{32}P$ for use as a screening probe using the procedure discussed above in Example 2.

Figure 5:
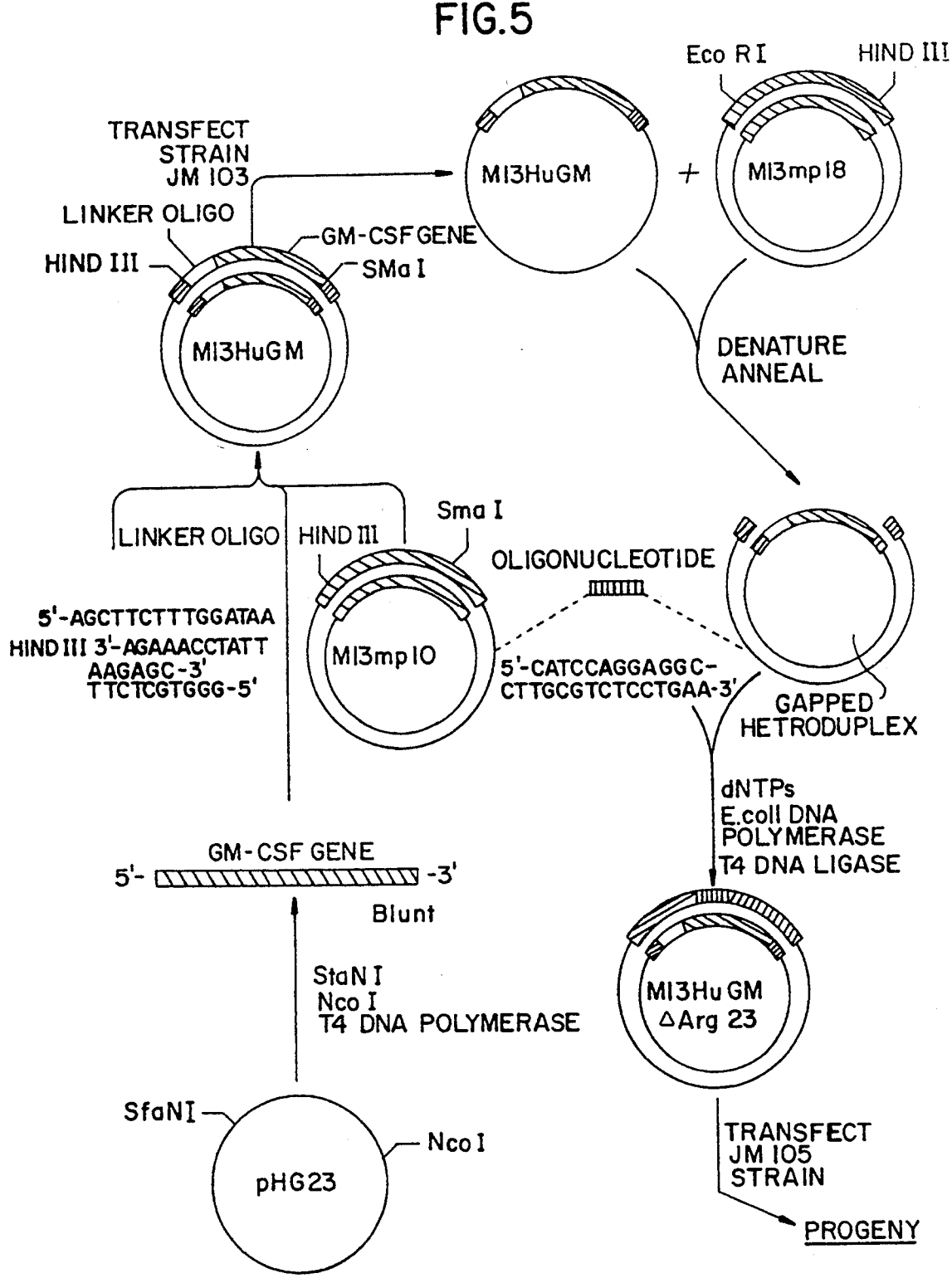

As illustrated in FIG. 5, the MCD5-24 oligonucleotide is employed together with the single-stranded template containing the wild-type GM-CSF gene prepared in Example 1 and with the M13 HuGM phage vector from Example 3 above to produce a gaped heteroduplex structure similar to that illustrated in FIG. 3 by use of the procedures set forth in Example 3. Thereafter, the gap-filled duplex structure is employed to transfect competent JM105 *E. coli* cells (Bethesda Research Laboratories, Bethesda, Md.) by standard techniques, as set forth in the Amersham Handbook, Supra. Screening for the mutated gene in the transfected JM105 cells is carried out using the procedure set forth in Example 4, and the nucleic acid sequence of the screened mutated gene, designated as M13HuGm ΔArg23 is ascertained using the chain-termination method set forth in Example 5.

Figure 6:
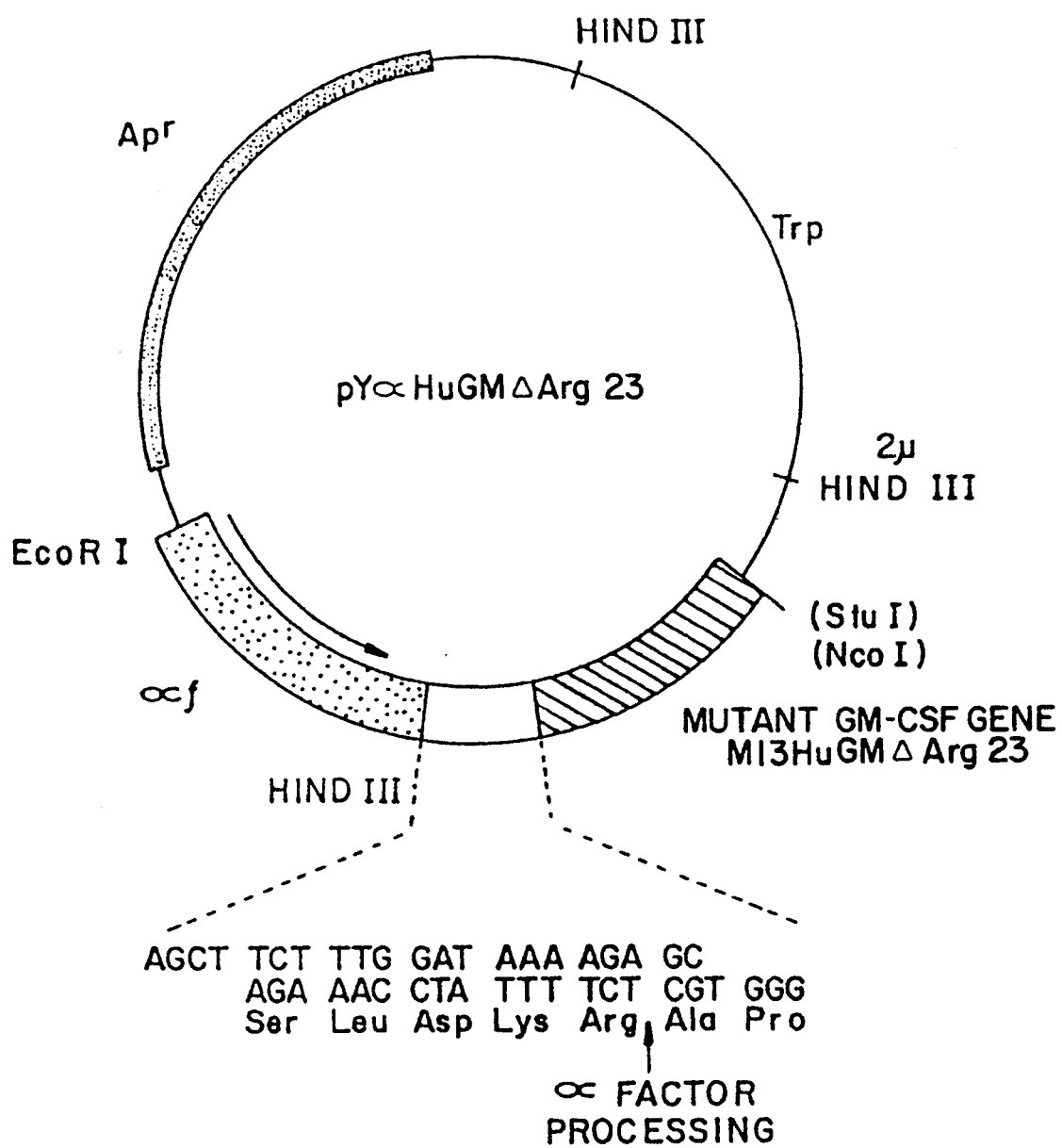

Analog GM-CSF is expressed using the procedure set forth in Example 6 wherein the 5' leader sequence, the coding region and a portion of the 3' flanking region of the mutant GM-CSF gene (from nucleotide members −6 to 502, is removed from the mutagenisis vector M13HuGM Δ Arg23 by digestion with a restriction enzyme Nco I followed by treatment with T4 DNA polymerase and then cleavage with Hind III. The resulting 505 bp M13HuGM Δ Arg23 DNA fragment with the 5' leader sequence attached hereto is isolated by gel electrophoresis and then ligated into the pYαf vector prepared by removal of the Hind 3- Stu I/Nco I section from the pYα fGM-2 expression plasmid (FIG. 5) (ATCC No. 53157) by standard techniques. The resulting pYα FHuGM Δ Arg23 expression plasmid (FIG. 6) is transformed into yeast strain 79 as detailed in Example 6 and then the expressed recombinant GM-CSF product tested for biological activity using the bone marrow colony assay set forth in Example 7.

As will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples contained in the foregoing description.

What is claimed is:

1. A polypeptide possessing human granulocyte-macrophage colony stimulating activity and comprising a sequence of amino acids which is identical to that shown as $Ala^1$ to $Glu^{127}$ in FIG. 1A but for the deletion or replacement by a non-basic amino acid of at least one of $Arg^{23}$ and $Arg^{24}$.

2. A polypeptide according to claim 1, wherein the arginine residue occupying position No. 23 has been replaced with a non-basic amino acid residue.

3. A polypeptide according to claim 1, wherein the arginine residue occupying position No. 24 has been replaced with a non-basic amino acid residue.

4. A polypeptide according to claim 3, wherein the arginine residue occupying position No. 24 has been replaced with a Leu residue.

5. A polypeptide according to claim 1, wherein the arginine residue occupying position No. 23 has been deleted.

6. A polypeptide according to claim 1, wherein the arginine residue occupying position No. 24 has been deleted.

7. A polypeptide according to any one of claims 1-6, wherein the amino acid sequence further comprises a sequence of amino acid residues extending from residue No. −4 to residue No. −1, which sequence is $$\underset{Cys}{-4} \quad \underset{Ser\ Ile\ Ser.}{\quad} \underset{}{-1}$$

8. A polypeptide according to any one of claims 1-6 wherein the amino acid sequence further comprises a sequence of amino acid residues extending from residue No. −5 to residue No. −1, which sequence is $$\underset{Ser}{-5} \quad \underset{Leu\ Asp\ Lys\ Arg.}{\quad} \underset{}{-1}$$

* * * * *